United States Patent [19]

Huang et al.

[11] 4,056,442

[45] Nov. 1, 1977

[54] LIPASE COMPOSITION FOR GLYCEROL ESTER DETERMINATION

[75] Inventors: Charles Y. Huang, S. Pasadena, Calif.; Alejo V. Roy, Carmel, Ind.

[73] Assignee: The Dow Chemical Company, Midland, Mich.

[21] Appl. No.: 691,932

[22] Filed: June 1, 1976

[51] Int. Cl.$^2$ .................... C07G 7/02; G01N 31/14
[52] U.S. Cl. .................................. 195/62; 195/63; 195/99; 195/103.5 R; 424/2
[58] Field of Search ............... 195/99, 103.5 R, 62, 195/63; 424/2

[56] References Cited

U.S. PATENT DOCUMENTS

| 3,759,793 | 9/1973 | Stork et al. | 195/99 X |
|---|---|---|---|
| 3,862,009 | 1/1975 | Wahlefeld et al. | 195/103.5 R |
| 3,898,130 | 8/1975 | Komatsu | 195/103.5 R |

OTHER PUBLICATIONS

Benzonana; G., Some Properties of an Exocellular Lipase from *Rhizopus arrhizirs* & Lipids, vol. 9, No. 3, 1974, (pp. 166–172).

*Primary Examiner*—David M. Naff
*Attorney, Agent, or Firm*—James W. Ambrosius

[57] ABSTRACT

A synergistic composition of microbial lipases from *Rhizopus arrhizirs* and *Candida cylindracea* is used for the hydrolysis of glycerol esters such as triglycerides in the determination of glycerol esters present in an aqueous medium such as body fluid.

13 Claims, 2 Drawing Figures

LIPASE COMPOSITION FOR GLYCEROL ESTER DETERMINATION

BACKGROUND OF THE INVENTION

The quantitative determination of mono-, di-, and particularly triglycerides in the body fluids of animals and man has been used in the clinical diagnosis of many diseases or disorders such as artherosclerosis, diabetes mellitus, nephrosis, biliary obstruction, and various metabolic derangements due to endocrine disturbances. Clinical analysis generally requires that the glycerol esters first be hydrolyzed to liberate glycerol and the corresponding fatty acids. Various techniques known in the art such as spectrophotometry are then used to determine the amount of glycerol or fatty acids released by the hydrolysis.

Until recently all of the methods used for the hydrolysis of triglycerides in a body fluid such as serum split the glycerol esters with a strong alkaline solution such as sodium or potassium hydroxide or, alternatively, employed a transesterification agent. These methods required the tedious and time-consuming separation of the lipids from the other serum constituents prior to hydrolysis and were not satisfactory for rapid routine clinical analysis. Recently, a number of enzymatic techniques have been developed for the hydrolysis of serum triglycerides. However, despite the convenience of enzymatic techniques compared to the older methods a number of problems remain.

The first lipase tried in the hydrolysis of serum triglycerides was pancreatic lipase which is isolated from the mammalian pancreas. This enzyme was found to be unsatisfactory because it was unable to completely hydrolyze the serum triglycerides in a reasonable period of time. A lipase isolated from the mold *Rhizopus arrhizus* (*R. arrhizus*) has been shown to completely hydrolyze the serum triglycerides within a relatively short period of time. U.S. Pat. No. 3,759,793. The free glycerol was then determined by a series of enzymatic reactions. This technique suffered from a number of disadvantages. A rather large amount of a highly purified *R. arrhizus* lipase (280 units of lipase to hydrolyze the triglycerides in a 10 microliter serum sample) was required to carry out the complete hydrolysis of the serum triglycerides. The quantities of purified *R. arrhizus* lipase required, make this procedure prohibitively expensive for routine clinical analysis. In addition, the system disclosed was not suitable for a one-step analysis procedure.

A mixture of a lipase, preferably a microbial lipase, with a protease has also been used to completely hydrolyze serum triglycerides. U.S. Pat. No. 3,703,591. The purity of the lipase used continued to have a significant effect on the efficiency of hydrolysis. U.S. Pat. No. 3,862,009 teaches that the hydrolytic efficiency of *R. arrhizus* lipase can be improved by carrying out the saponification in the presence of a carboxylesterase and of an alkali metal or alkaline earth metal alkyl sulfate. U.S. Pat. No. 3,898,130 discloses a method for the rapid hydrolysis of triglycerides using a combination of a pancreatic lipase, a microbial lipase, and a bile salt. All three components are essential for the process to operate effectively.

SUMMARY OF THE INVENTION

The present invention is directed to a unique combination of two microbial lipases which are capable of rapidly and completely hydrolyzing the glycerol esters present in an aqueous medium such as a body fluid or foodstuff. It has been found that a combination of the lipases from *R. arrhizus* and *Candida cyclindracea* (*C. cylindracea*) produce a synergistic effect which overcomes many of the disadvantages inherent in methods known in the prior art. Using the combination of lipases and the method of the present invention, it is possible to completely hydrolyze the glycerol esters present in an aqueous medium using relatively small amounts of the readily available commercial grade lipases. This method also makes possible for the first time a single reagent which can be used for the colorimetric determination of serum triglycerides. Thus, this invention makes possible a simple, convenient, and rapid method for determining serum triglycerides in clinical laboratories.

An object of the present invention is to provide an inexpensive and practical enzymatic method for the hydrolysis of glycerol esters in an aqueous medium. It is also an object of the invention to provide an enzymatic composition which will completely hydrolyze glycerol esters in an aqueous medium in a short period of time. It is a further object of this invention to provide a reagent composition and method of use that is suitable for routine clinical analysis for the determination of glycerol esters in a body fluid. It is further an object of the invention to provide a convenient colorimetric method for the determination of serum triglycerides.

As used in the present specification and claims, the term body fluid refers to any aqueous body fluid which contains mono-, di-, or triglycerides. The body fluid can be an extract, as from a tissue homogenate or the like, or it can be a body fluid such as blood, serum, plasma, lymphatic fluid, cerebrospinal fluid or the like.

It is seen from the foregoing description that the present invention is directed to a unique composition and method of hydrolyzing serum triglycerides prior to the determination of glycerol or fatty acids. This method may be used in combination with any of the known procedures for quantitatively determining the amount of glycerol or fatty acids present, or it may be used as part of the unique colorimetric system disclosed herein. Thus, as will be explained this invention is particularly useful when used in a single step colorimetric analysis of serum triglycerides.

DESCRIPTION OF DRAWINGS

Referring to the drawings.

DETAILED DESCRIPTION OF THE INVENTION

Figure 1:
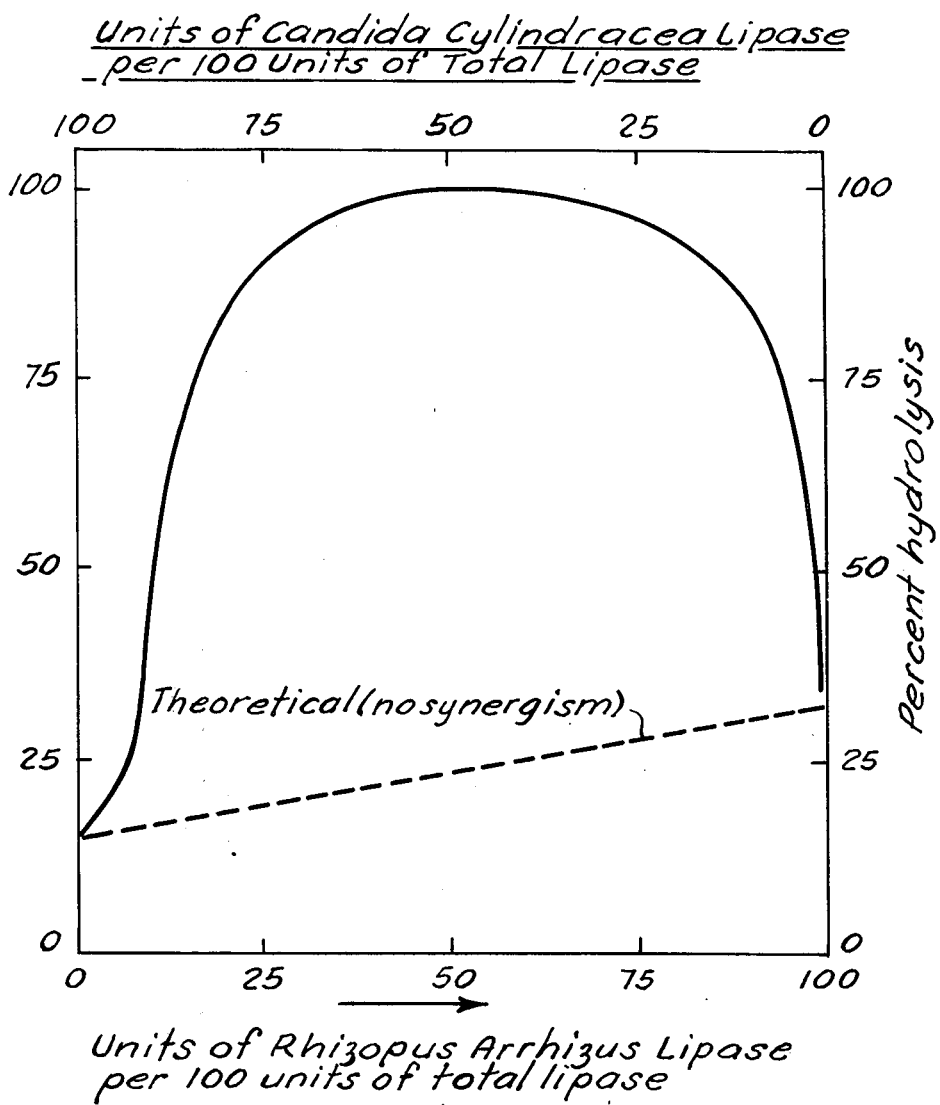
FIG. 1 demonstrates graphically the synergistic effect of a mixture of *R. arrhizus* and *C. cylindracea* lipases with varying proportions of lipases in the mixture.

In general, it has been found that a synergistic mixture of the two lipases containing from about 15 to 95 units of *R. arrhizus* lipase and from about 85 to 5 units of *C. cylindracea* lipase per 100 units of total lipase present gives good hydrolysis. A mixture containing from about 35 to 80 units of *R. arrhizus* lipase and from 65 to 20 units of *C. cylindracea* lipase per 100 units of total lipase is preferred in that such mixtures give substantially complete hydrolysis under ordinary test conditions.

Optimal hydrolysis of the triglycerides present in an aqueous media occurs when the ratio of *C. cylindracea* lipase to *R. arrhizus* lipase is about 0.9. In the hydrolysis of the triglycerides present in a 25 microliter sample of human serum a mixture of 70 units of *R. arrhizus* lipase to 64 units of *C. cylindracea* lipase was found to give optimum results at 37° C at a pH of 7.6. An increase in the amount of either lipase in the above combination did not materially affect the enzymatic hydrolysis of the serum triglycerides. A decrease in the units of either lipase present resulted in incomplete hydrolysis of the serum triglycerides within the incubation period of the test. Therefore, substantial deviation from the optional proportions of the lipase combination will result in either an increase in the incubation time required to achieve complete hydrolysis or incomplete hydrolysis of the triglycerides.

The exact proportions of the individual lipases in the composition of the present invention will vary somewhat depending upon the particular application desired. For example, if the pH of the reaction is changed, the amount of the lipases as well as their ratio in the composition will also change if optimum hydrolysis is desired. It is also understood that if a faster reaction is desired, the amount of lipase present can be simply increased. Likewise if a longer incubation time is desired, the amount of lipases required to hydrolyze the triglycerides is decreased. As used here, a unit of lipase activity is the amount of fatty acid neutralized by one micromole of sodium or potassium hydroxide in one minute at 25° C at a pH of 8.1 and 8.9 for *C. cylindracea* lipase and *R. arrhizus* lipase, respectively.

Enzymatic hydrolysis using the lipase composition of the invention can be carried out within a pH range of from about 5.5 to 9.0. The optimal pH for the determination of triglycerides present will be dependent on the particular enzymatic scheme used to carry out the analysis of glycerol or fatty acids released by the hydrolysis. Thus, the present invention may be readily adapted to a number of analytical procedures. A temperature of 37° C was found to give satisfactory hydrolysis under the conditions used in this procedure. Lower temperatures are also operable but require longer incubation times to achieve complete hydrolysis. Higher temperatures will destroy the enzyme. The exact incubation time required to achieve complete hydrolysis will depend upon the exact procedure employed to determine the glycerol and fatty acids released by hydrolysis, the pH of the media, the sample size, the incubation temperature, and the exact ratio of lipases employed. In general, an incubation time of from about 7 to 10 minutes was found to give complete hydrolysis at a pH of 7.6, at a temperature of 37° C when 70 units of *R. arrhizus* lipase and 64 units of *C. cylindracea* lipase were mixed with 20 to 40 microliters of human serum.

A lipase combination containing 70 units of *R. arrhizus* and 64 units of *C. cylindracea* was found to completely hydrolyze the lipids present in a 25 microliter sample of human serum up to a triglyceride concentration of about 1100 mg/dl. Thus, an efficient analytical procedure for the determination of serum triglycerides using the present invention will be linear up to this triglyceride concentration.

Various procedures are available for the determination of glycerol released by the hydrolysis of the lipids. One method uses the glycerol to convert adenosine triphosphate to adenosine diphosphate in the presence of glycerokinase. The adenosine diphosphate then is used to convert phosphoenol pyruvate to pyruvate. By following the decrease in absorbance which results when nicotinamide-adenine-dinucleotide is converted to its oxidized form in the presence of pyruvate the amount of glycerol present in the medium can be determined. Another method of determining the amount of glycerol present in the medium which can be used in combination with the lipase composition described above to give a single-step colorimetric method which uses the conversion of glycerol to glycerol-1-phosphate by adenosine-5'-triphosphate, hereafter ATP, to generate reduced nicotinamide-adenine-dinucleotide, hereafter NADH, from its oxidized form, hereafter called NAD. The NADH is then used to reduce a tetrazolium salt to its reduced chromophor. Usually the tetrazolium salt used is 2-p-iodophenyl-3-nitrophenyl-5-phenyltetrazolium chloride or INT. This method is also advantageous because the production of the chromogen may be followed on a conventional clinical grade colorimeter. Thus by measuring the amount of color produced, the amount of glycerol present may be determined. The general reaction sequence is summarized by the following reactions.

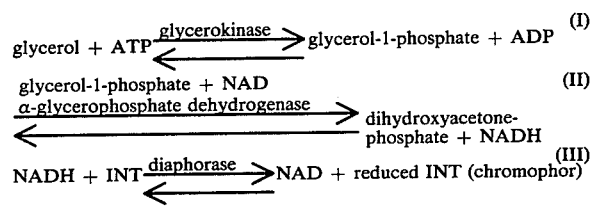

The amount of color developed by the above reaction sequence is directly proportional to the triglyceride concentration when hydrolyzed by the method and composition of the present invention.

The following examples further describe the use of the present invention when employed in the determination of triglycerides in human serum, but these examples are not to be construed as a limitation on the present invention.

EXAMPLE 1

A preferred reagent composition which is suitable for the colorimetric determination of the triglycerides in human serum contains the following.

| | |
|---|---|
| Magnesium Chloride | 0.06% w/v |
| Adenosine-5'-triphosphate | 0.18% w/v |
| Nicotinamide Adenine Dinucleotide (NAD) | 0.72% w/v |
| 2-(p-indophenyl)-3-p-nitrophenyl-5-phenyl Tetrazolium Chloride | 0.025% w/v |
| Diaphorase | 5.52 U/test |
| Glycerol Kinase | 0.92 U/test |
| α-Glycerol Phosphate Dehydrogenase | 13.8 U/test |
| Lipase (from *Rhizopus arrhizus*) | 70 U/test |
| Lipase (from *Candida cylindracea*) | 64 U/test |
| Sodium Chloride | 0.1 mol/liter |
| Calcium Chloride | 5 mmol/liter |
| Ethylenediamine Tetracetic Acid (EDTA) | 0.5 mmol/liter |

All the above constituents are dissolved in a tris (hydroxymethyl) amino methane (TRIS) buffer (0.1 mol/liter, pH 7.6). Preferably the first 9 of the above ingredients are combined in a lyophilized mixture in order to increase stability. The remaining three ingredients are dissolved in the TRIS buffer having a pH of about 7.6.

EXAMPLE 2

A general procedure for carrying out a triglyceride determination on human serum is as follows:

The lyophilized substrate of Example 1 above is reconstituted using 1 ml of the pH 7.6 TRIS buffer. After prewarming the solution thus obtained at 37° C for about 5 minutes 20–25 ul of serum is added. The serum mixture is incubated for about 10 minutes and the tubes are removed from the heat source. Usually the final volume of the sample is adjusted to about 3 ml with 0.05N hydrochloric acid. Readings may be taken in a spectrophotometer or a colorimeter set at a wavelength of about 500 nanometers. The color developed is directly proportional to the triglyceride concentration.

EXAMPLE 3

Ten samples of human sera with a wide range of triglyceride concentrations were analyzed using a conventional chemical hydrolysis with sodium hydroxide in methanol. The same samples were analyzed using the enzymatic composition and method described in Examples 1 and 2, respectively. A comparison of the results obtained using the two methods is shown in Table I. The results indicate that the hydrolysis of the triglycerides in the sera samples by the lipase composition was comparable to the hydrolysis obtained by saponification.

Table I

| Serum Sample Number | Triglyceride Concentrations (mg/dl) | |
|---|---|---|
| | Chemical Hydrolysis | Enzymatic Hydrolysis |
| 1 | 134 | 128 |
| 2 | 63 | 62 |
| 3 | 215 | 234 |
| 4 | 313 | 313 |
| 5 | 305 | 305 |
| 6 | 691 | 681 |
| 7 | 23 | 23 |
| 8 | 151 | 161 |
| 9 | 347 | 343 |
| 10 | 404 | 418 |

EXAMPLE 4

Human serum with a triglyceride concentration of about 560 mg/dl as determined by current chemical saponification methods was analyzed using the reagent of Example 1, except that the lipase from *R. arrhizus* was varied from 0 to 140 units per test. The sample size used in each test was 25 ul. The general procedure of analysis was as described in Example 2. The results are shown in Table 2. Under the conditions of this test, the results indicate that with 64 units of *C. cylindracea* lipase per test complete hydrolysis is achieved in ten minutes when 70 units of *R. arrhizus* lipase is present.

Table 2

| Rhizopus arrhizus Lipase Concentration Units/Test | Degree of Hydrolysis |
|---|---|
| 0 | 14.8% |
| 3.5 | 22.8% |
| 7.0 | 30.8% |
| 17.5 | 85.9% |
| 35.0 | 97.0% |
| 70.0 | 100.0% |
| 140.0 | 100.0% |

EXAMPLE 5

This procedure was the same as used in Example 4 above except that the concentration of *C. cylindracea* lipase was varied from 0 to 64 units per test, while the *R. arrhizus* lipase concentration was constant at 70 units per test. As shown in the results in Table 3, complete hydrolysis of the triglycerides was achieved when 64 units of *C. cylindracea* lipase was present in the reagent composition.

Table 3

| Candida Cylindracea Lipase Concentration Units/Test | Degree of Hydrolysis |
|---|---|
| 0 | 33.7% |
| 2.1 | 65.8% |
| 6.4 | 83.3% |
| 10.7 | 92.8% |
| 21.4 | 95.4% |
| 42.8 | 97.9% |
| 64.0 | 100.0% |

The data from Tables 1 and 2 are presented graphically in FIG. 1. The various lipase concentrations are expressed as units of *R. arrhizus* and *C. cylindracea* lipase per 100 units of total lipase mixture. Theoretical activity of the various lipase mixtures if no synergism were present is shown as a dotted line on the graph.

EXAMPLE 6

Using the general procedure outlined above with a reagent composition similar to that of Example 1 except that no *C. cylindracea* lipase was present various concentrations of *R. arrhizus* lipase were used to hydrolyze the triglycerides present in a serum sample having about 530 mg/dl of triglycerides. The results are presented graphically in FIG. 2. The data indicate that without any *C. cylindracea* lipase present, the *R. arrhizus* lipase can be increased 10 fold, i.e. up to 700 units, without obtaining complete hydrolysis of the triglycerides.

EXAMPLE 7

The procedure of Example 6 above was repeated with various concentrations of *C. cylindracea* lipase present in the reagent and no *R. arrhizus* lipase present. The results of this study also shown graphically in FIG. 2 indicate that without *R. arrhizus* lipase present in the mixture a five fold increase in *C. cylindracea* lipase concentration, i.e. up to 320 units, hydrolyzes less than 20% of the triglycerides present.

Figure 2:
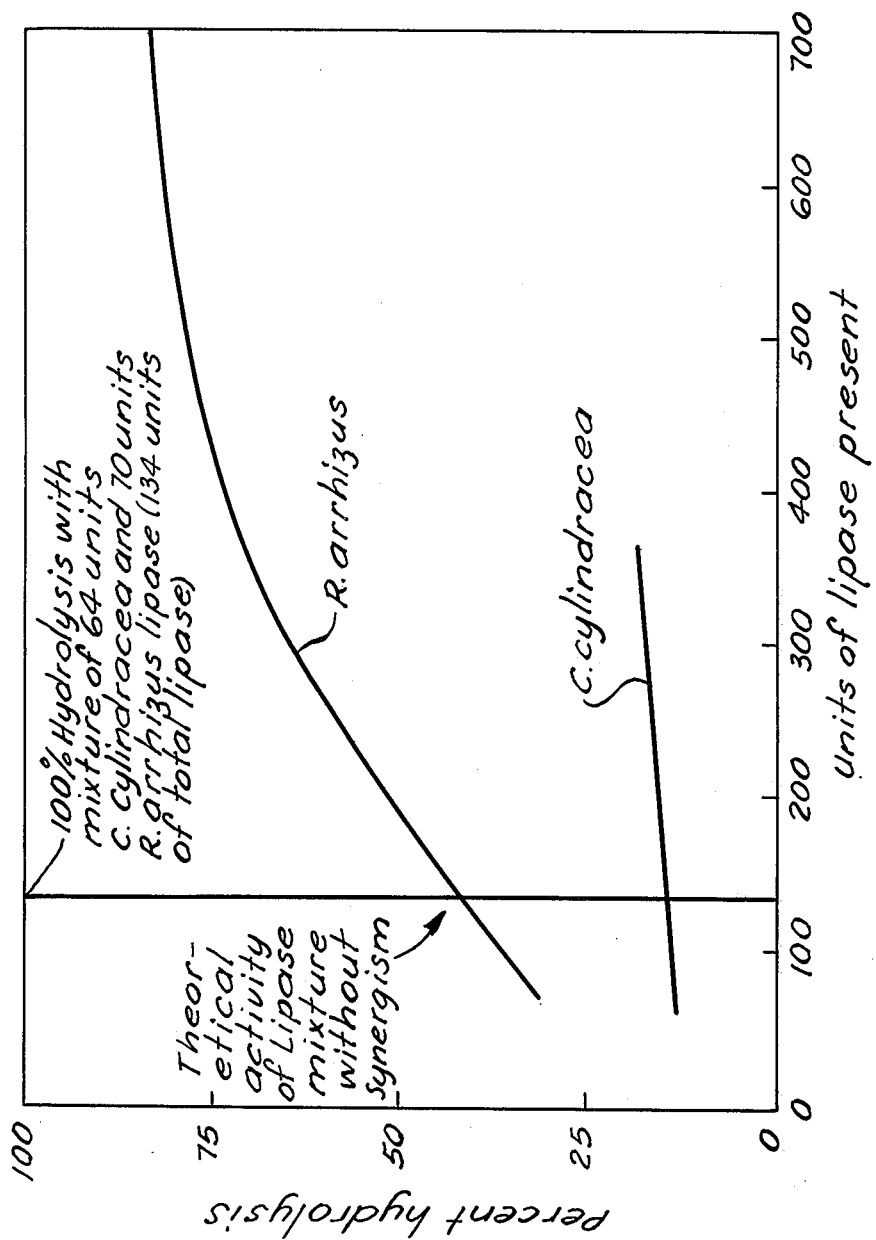
FIG. 2 shows the effect of various concentrations of the individual lipases compared with the hydrolysis achieved with a synergistic composition of both lipases.

The results of Examples 6 and 7 are contrasted in FIG. 2 with the complete hydrolysis of the triglycerides present in the serum sample when a synergistic composition containing only 134 total units of lipase was used. The synergistic effect of the lipase mixture which contained 70 units of *R. arrhizus* and 64 units of *C. cylindracea* will be understood when it is realized that the theoretical additive effect of the two lipases if no synergistic effect were present would only hydrolyze about 45% of the triglycerides in the serum. Yet as a result of the synergism, complete hydrolysis was achieved.

I claim:

1. A composition useful for the hydrolysis of a glycerol ester in an aqueous medium comprising a mixture of from 15 to 95 units of *Rhizopus arrhizus* lipase and from 5 to 85 units of *Candida cylindracea* lipase per 100 units of total lipase present.

2. The composition of claim 1 wherein the composition contains from about 35 to 80 units of *Rhizopus arrhizus* lipase and from about 20 to 65 units of *Candida cylindracea* lipase per 100 units of total lipase present.

3. The composition of claim 2 wherein the ratio of *Candida cylindracea* lipase to *Rhizopus arrhizus* lipase is 0.9.

4. A reagent composition useful for the determination of triglyceride concentration in serum by measuring the light absorbance of the serum following hydrolysis of the triglycerides to glycerol and fatty acids which comprises an enzyme mixture having from 15 to 95 units of *Rhizopus arrhizus* lipase and from 5 to 85 units of *Candida cylindracea* lipase per 100 units of total lipase and chemical means for measurably changing the spectroscopic absorbance of the composition in proportion to the amount of glycerol released in the serum.

5. The reagent composition of claim 4 which contains adenosine-5-triphosphate, glycerokinase, phosphoenol pyruvate, and nicotinamide-adenine-dinucleotide.

6. The reagent composition of claim 4 which contains adenosine-5'-triphosphate, nicotinamide-adenine-dinucleotide, a tetrazolium salt, glycerokinase, α-glycerophosphate dehydrogenase, and diaphorase.

7. The lyophilized composition of claim 6.

8. A method for hydrolyzing a glycerol ester and for determining the amount of glycerol ester present in an aqueous medium which comprises incubating the glycerol ester at a pH of 5.5–9.0 with a lipase mixture having the proportions of 15 to 95 units of a lipase from *Rhizopus arrhizus* and 5 to 85 units of a lipase from *Candida cylindracea* per 100 units of total lipase present for a time sufficient to hydrolyze the glycerol ester and determining the amount of glycerol or fatty acids released by the hydrolysis.

9. The method of claim 8 wherein the aqueous medium is a body fluid.

10. The method of claim 9 wherein the body fluid is serum.

11. The method of claim 10 further comprising determining the amount of glycerol released by the hydrolysis.

12. The method of claim 11 wherein the gycerol is determined by reacting the glycerol in the serum with adenosine-5-triphosphate in the presence of glycerokinase to form glycerol-1-phosphate, reacting the glycerol-1-phosphate with nicotinamide-adenine-dinucleotide in the presence of α-glycerophosphate dehydrogenase to form reduced nicotinamide-adenine-dinucleotide, reducing a tetrazolium salt with the reduced nicotinamide-adenine-dinucleotide, and measuring the color produced.

13. The method of claim 12 wherein the tetrazolium salt is 2-p-indophenyl-3-p-nitrophenyl-5-phenyltetrazolium chloride.

* * * * *